(12) United States Patent
Emerson

(10) Patent No.: US 6,858,822 B1
(45) Date of Patent: Feb. 22, 2005

(54) SURFACE ANALYSIS PRECEDING ELECTROFUSION OF THERMOPLASTICS

(75) Inventor: Dave Emerson, 2095 W. Union Chapel Rd., Nixa, MO (US) 65714

(73) Assignee: Dave Emerson, Nixa, MO (US)

( * ) Notice: Subject to any disclaimer, the term of this patent is extended or adjusted under 35 U.S.C. 154(b) by 0 days.

(21) Appl. No.: 10/634,652

(22) Filed: Aug. 4, 2003

Related U.S. Application Data
(60) Provisional application No. 60/400,488, filed on Aug. 2, 2002.

(51) Int. Cl.$^7$ ................................................. H05B 3/58
(52) U.S. Cl. ........................ 219/535; 219/221; 219/230; 219/544
(58) Field of Search ................................. 219/520, 535, 219/544, 221, 227–230, 243; 73/866.5, 104–105; 285/21.1, 21.2, 331; 156/274.2, 294, 304.2

(56) References Cited

U.S. PATENT DOCUMENTS

| | | | |
|---|---|---|---|
| 3,973,441 A | | 8/1976 | Porter ........................ 73/432 R |
| 4,213,331 A | | 7/1980 | Porter ........................... 73/105 |
| 4,435,829 A | * | 3/1984 | Siler et al. ..................... 378/60 |
| 4,639,580 A | | 1/1987 | Johnson ...................... 219/541 |
| 4,663,794 A | | 5/1987 | Evans ...................... 15/104.04 |
| 5,116,082 A | | 5/1992 | Handa et al. .................. 282/21 |
| 5,311,785 A | * | 5/1994 | Bar-Shay .................... 73/866.5 |
| 5,369,248 A | * | 11/1994 | Dufour et al. ............... 219/541 |
| 5,800,247 A | * | 9/1998 | Harms ............................ 451/5 |
| 5,824,179 A | * | 10/1998 | Greig ....................... 156/274.2 |
| 5,911,895 A | * | 6/1999 | Porfido et al. ............... 219/221 |
| 6,062,948 A | | 5/2000 | Schiff et al. .................... 451/9 |

FOREIGN PATENT DOCUMENTS

| | | | | |
|---|---|---|---|---|
| JP | 07128305 A | * | 5/1995 | .......... G01N/29/04 |

OTHER PUBLICATIONS

Product Specification of electrofusion fittings of INNOGAZ® (of Monaco), product Nos. PE 2406 through PE 3408, dated 01–99 (2 sheets).
Operating Manual for the Phoenix™ Electrofusion Processor of EF Technologies, Inc. (Of Newark, Delaware). published earlier than Aug. 2, 2002 (entire manual, comprising pp. 1–40 & front & back covers).
Product data for Lasercheck® gauge of the Optical Dimensions Co. (of Lake Forest, California), dated May 23, 2000 (6 sheets), from www.opticaldimensions.com.

* cited by examiner

*Primary Examiner*—Tu Hoang
(74) *Attorney, Agent, or Firm*—Jonathan A. Bay

(57) ABSTRACT

A method and apparatus achieves making a surface-analysis determination precedent to allowing an electrofusion welding operation on pipe stock which is prescribed to be scraped, skinned or cleaned of surface contaminants prior to being graded 'passable' for such electrofusion welding. The method and apparatus utilizes non-contacting probes affixed to the welding power-supply leads such that inspection is automatic on the applicable pipe section(s) contemporaneously prior to enabling power-supply to the hot-wire welding coils. If the applicable pipe section fails the inspection, the welding equipment is disabled until the probes are disassembled, and then re-assembled for a succeeding inspection, such that during the interim an operator presumptively rectifies the situation as by re-scraping or skinning the applicable pipe section.

1 Claim, 11 Drawing Sheets

US 6,858,822 B1

SURFACE ANALYSIS PRECEDING ELECTROFUSION OF THERMOPLASTICS

CROSS REFERENCE TO PROVISIONAL APPLICATION(S)

This application claims the benefit of U.S. Provisional Application No. 60/400,488, filed Aug. 2, 2002, which is incorporated herein in full by this reference.

BACKGROUND AND SUMMARY OF THE INVENTION

The invention relates to electrofusion of thermoplastics and, more particularly, to apparatus and method for making a pipe-surface quality determination preceding electrofusion.

Nowadays thermoplastic fittings are commonly fused or welded to thermoplastic pipes by electrofusion technology. Typically the fitting has an embedded conductor coiled inside it for induction heating by an electrofusion processor to accomplish welding to the pipe. It generally is a prerequisite that the involved pipe surface be cleaned and scraped preceding electrofusion. Scraping importantly accomplishes exposing unvarnished and/or fresh plastic for the electrofusion process. Un-scraped or insufficiently scraped pipe exacerbates problems with achieving leak-tight electrofusion welds. In cases of natural gas piping, leaking natural gas is a tremendous hazard.

To date reliance on whether the pipe is sufficiently scraped preceding electrofusion is reliant wholly on the honesty and/or good judgment of the responsible worker.

It is an object of the invention to provide a machine-controlled determination of pipe surface quality preceding electrofusion of thermoplastics in order to eliminate human error.

A number of additional features and objects will be apparent in connection with the following discussion of preferred embodiments and examples.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the appended claims. In the drawings.

FIGS. 2a, 2b and 2c form a series of views showing an example, prior art, plastic pipe scraper in accordance with U.S. Pat. No. 4,663,794—Evans, which is incorporated by reference, wherein:

FIG. 2a is a side elevational view,

FIG. 2b is a bottom plan view thereof, and

FIG. 2c is a side elevational view comparable to FIG. 2a except showing the scraper in use to accomplish scraping on the exterior of plastic pipe, whereby the scraping process produces a series of spirally formed ridges and valleys proceeding axially along the exterior surface of the pipe;

FIGS. 3a/3b and FIG. 4 form a series of views showing a non-limiting selection of example electrofusion fittings in accordance with the prior art, wherein:

FIG. 3a is a side elevational view of tapping-tee fitting and its mating under saddle, which slides on the lips of the tapping-tee in the direction of the reference arrow until limited by stops.

DETAILED DESCRIPTION OF THE PREFERRED EMBODIMENTS

The invention relates to apparatus and methods as more particularly described below for making machine-controlled determination(s) of pipe surface quality preceding electrofusion of thermoplastics, and in order to promote elimination of human error.

Figure 1:
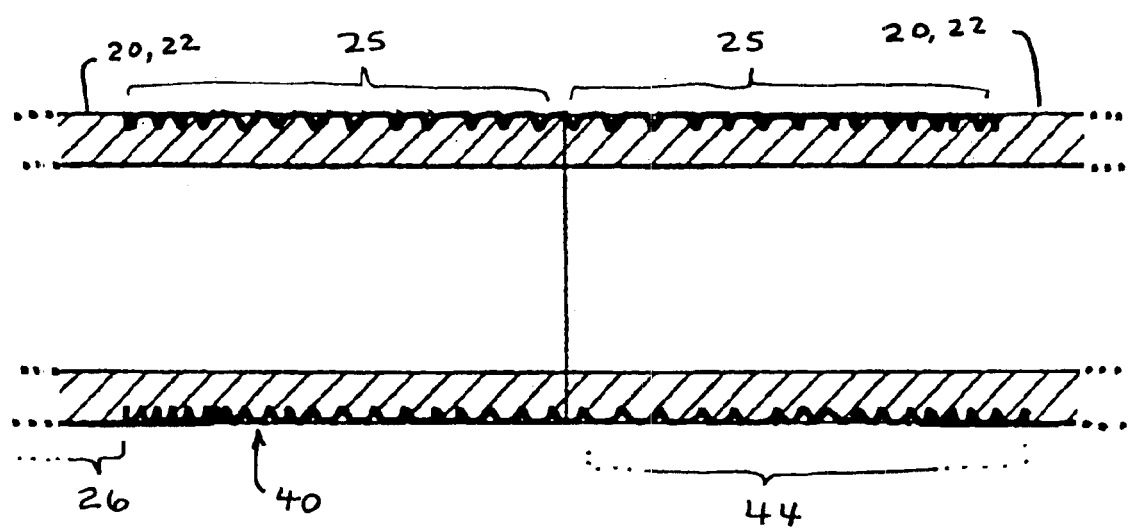
FIG. 1 is an elevational sectional view of two plastic pipe ends butted against one another for permanent joining together by electrofusion technology as known in the prior art, wherein the exterior surfaces of both pipe ends have been cleaned and scraped for a given marginal length extending away from each end such that the scraping exposes unvarnished and/or fresh plastic.
Figure 2A:
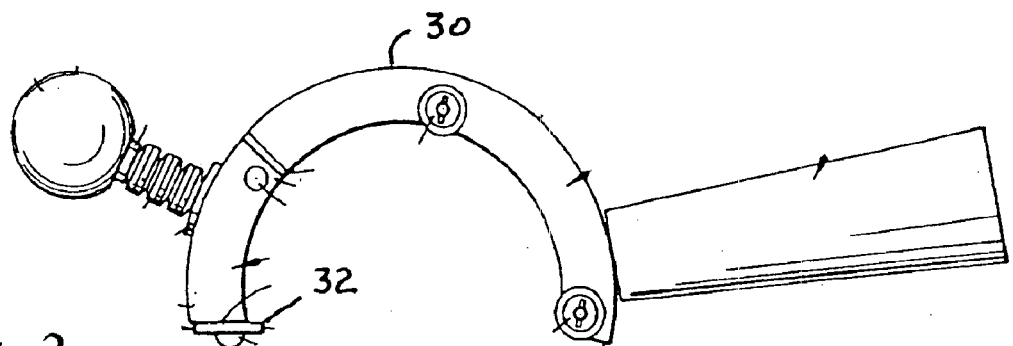
Figure 2B:
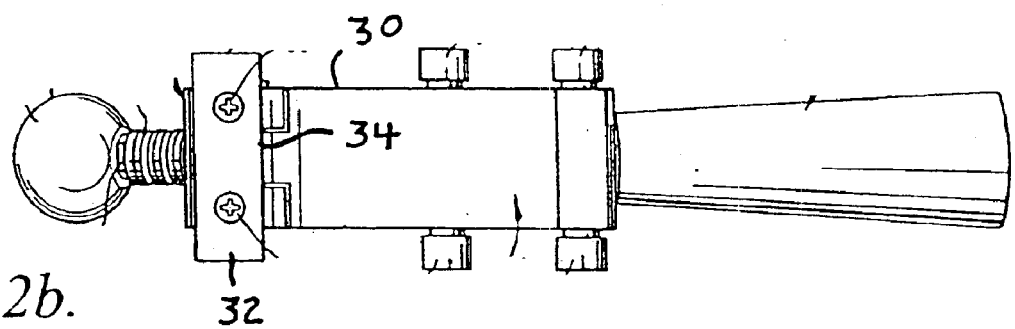
Figure 2C:
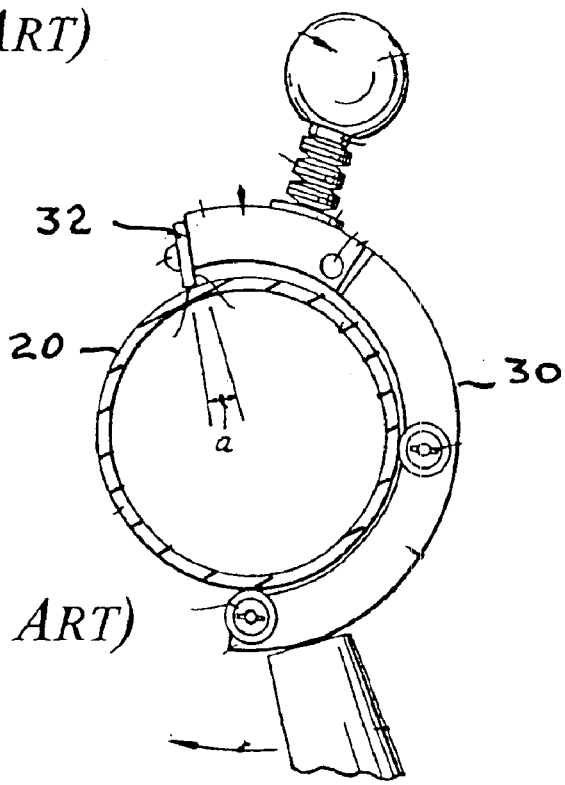

By way of background, briefly, electrofusion includes at least the practice of mating plastic parts 20 by the fusion achieved from the heat developed in hot-wire coil(s) (eg., 52b in FIG. 4) embedded in one or the other of the parts 50 (eg., typically embedded in a fitting 50, and see FIGS., 3a, 3b and/or 4). FIG. 1 shows the ends 22 of two plastic pipe 20 ends butted against one another in preparation for permanent joining together by electrofusion technology as known in the prior art (although that will require a 'coupling' fitting 50 as shown by, eg., as 52 in FIG. 4). The exterior surfaces of both pipe ends 22 have been cleaned and/or scraped (eg., skinned) for a given marginal length 25 extending away from each end 22 such that the scraping (or skinning) exposes newly-exposed plastic. FIGS. 2a, 2b and 2c are a series of views showing an example, prior art, plastic pipe scraper 30 and in accordance with U.S. Pat. No. 4,663,794-Evans.

In general, raw or un-scraped (un-skinned) pipe stock 26 is procured with a varnished or otherwise smooth finish that is unsuitable for electrofusion process(es) while in that raw or un-scraped (un-skinned) condition. That is, there is an unacceptable likelihood that an electrofusion joint will fail quality standards if obtained by plastic parts having any surface varnish or dirt if not oxidation or contamination or OEM printing thereon. Hence it has long been a practice in the industry to scrape off a skin- or surface-layer of the pipe 20 in order to expose fresh or clean plastic 25 which indeed is suitable for electrofusion process(es). Scrapers 30 typically have a blade 32 that is about ⅜-inch (~10 mm) wide and formed with about twelve shallow teeth 34 across such width such that as a result the scraper 30 might leave about thirty-two lines per inch (~twelve lines per cm) of helically-formed ridges (eg., indicated by reference numeral 40 in FIG. 8, and which are alternated of course by valleys) along the axial extension of the exterior surface of the pipe 20. The prior art scrapers 30 are arranged to auto-advance themselves helically along the axis of the pipe 20 while being turned in complete rotations so that the last furrow left behind by the trailing tooth of the blade 32 plows through the plastic skin more or less accurately parallel and properly spaced relative to the leading furrow cut or plowed one-rotation previously by the leading tooth. In other words, a scraped-section 25 of pipe 20 appears to be formed with a continuous screw thread (eg., as indicated by reference numeral 44 in FIG. 3), having a coarseness at about thirty-two lines per inch (~twelve lines per cm), although relatively finer and much more coarser teeth arrangement are also known in the art.

Additionally, the scraping typically produces a surface roughness of between about 200 microns ($\sim^5/1000^{ths}$ mm) and 500 microns ($\sim^{13}/1000^{ths}$ mm). In contrast, un-scraped sections 26 of the pipe 20 typically exhibit a much smoother finish, measuring for example at about 30 microns (very approximately $\sim^1/1000^{ths}$ mm), which despite being smoother is structurally disordered and not nearly as structurally ordered as scraped pipe 25, such structural ordering being (as said) in the form of, eg., screw thread 44.

Figure 3A:
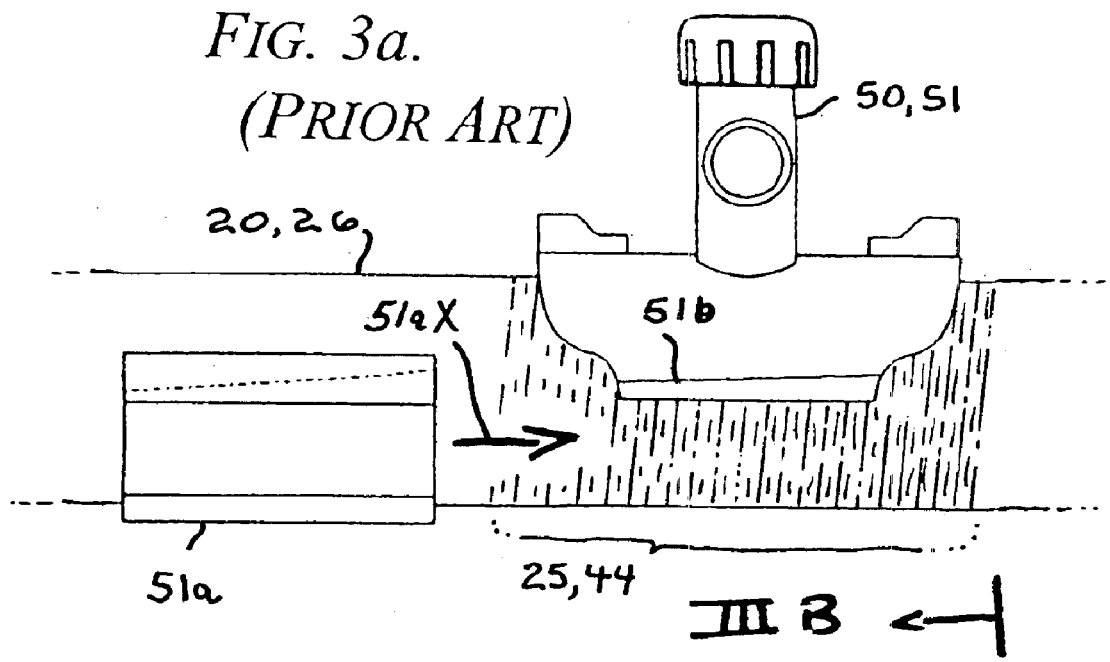
Figure 3B:
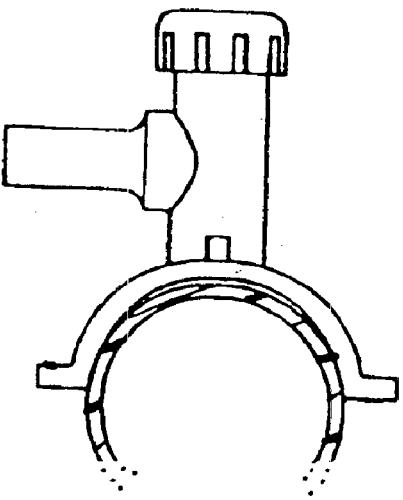
FIG. 3b is a view in the direction of arrows IIIB—IIIB in FIG. 3a except in the omitting the under saddle.

FIGS. 3a and 3b together show one example of a prior art electrofusion fitting 50, and that being a tapping-tee fitting 51. FIG. 3a shows the tapping tee fitting 51 situated on a section of scraped pipe 25, as prior to electrofusion. FIG. 3a also shows that the tapping-tee fitting 51 has a mating under saddle 51a, which slides on the lips 51b of the tapping-tee 51 in the direction of the reference arrow 51aX until limited by stops. The under saddle 51a is utilized predominantly for temporary clamping purposes only. As soon as the electro-fusion weld is completed, the under saddle 51a might be optionally removed as needless although it is typical to leave it in place. If the under saddle 51a were removed after welding, then FIG. 3b shows an axial view (ie., in the direction of arrows IIIB—IIIB in FIG. 3a) of how that would appear.

Figure 4:
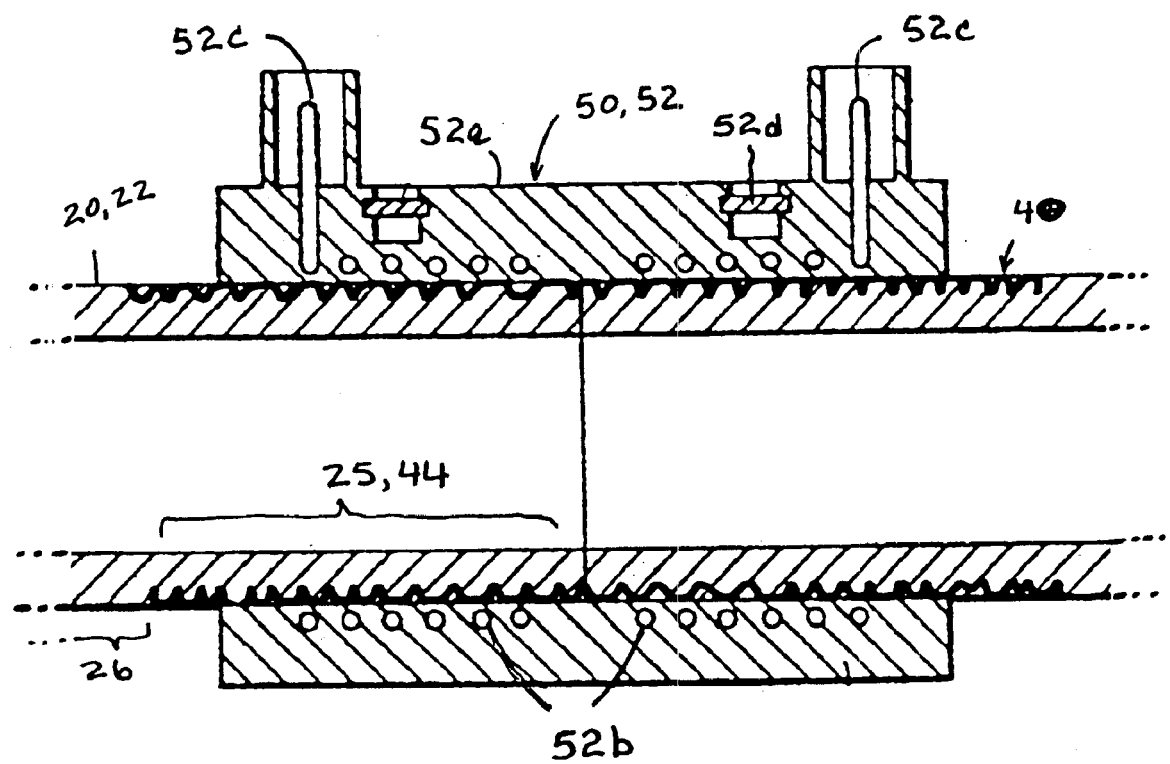
FIG. 4 is an elevational sectional view comparable to FIG. 1 except showing an electrofusion coupling fitting slid over the scraped end margins of the abutting pipe ends.

FIG. 4 shows a further example of an electrofusion fitting 50 in accordance with the prior art, this more particularly being a coupling fitting 52. Coupling fittings 52 receive insertion of the scraped end margins 25 of a pair of abutting pipe ends 22, such as comparably shown previously in FIG. 1. In FIG. 4, the fitting 52 has a barrel section 52a having an inner surface formed with an embedded hot-wire coil conductor 52b wound in a helix around the barrel section 52a and terminating in opposite terminals 52c. To weld, the terminals 52c are connected to connectors "C" (not shown but see, eg., what is denominated as "C" in FIG. 7) of an electrofusion processor (again not shown in this view but see what is denominated as EP100 in, eg., FIG. 7). The electrofusion processor EP100 supplies power to the terminals 52c through the connectors "C." How much power, and by what profile of power-against-time, is a matter which is highly fitting-specific. Notwithstanding, fitting manufactures widely disseminate such specifications for their fittings 50 and they even code their fittings accordingly, typically by way of a bar code. Prior art electrofusion processors (see for comparison, eg., FIG. 7) include readers of such bar codes by way of for example and without limitation a bar code wand "W" (not shown in FIG. 4 but see, eg., what is denominated as "W" in FIG. 7) in order to search through their memory for what power-against-time profiles are expected, and supply such. The fitting 52 in FIG. 4 furthermore includes a pair of visual ports 52d, which are alongside the pair of terminals 52c respectively. After the fitting 52 has been fused welded to form the pipe connection, the visual ports' 52d afford an operator opportunity to visually inspect the success (or not) of the weld. The foregoing are matters of the prior art.

Figure 5:
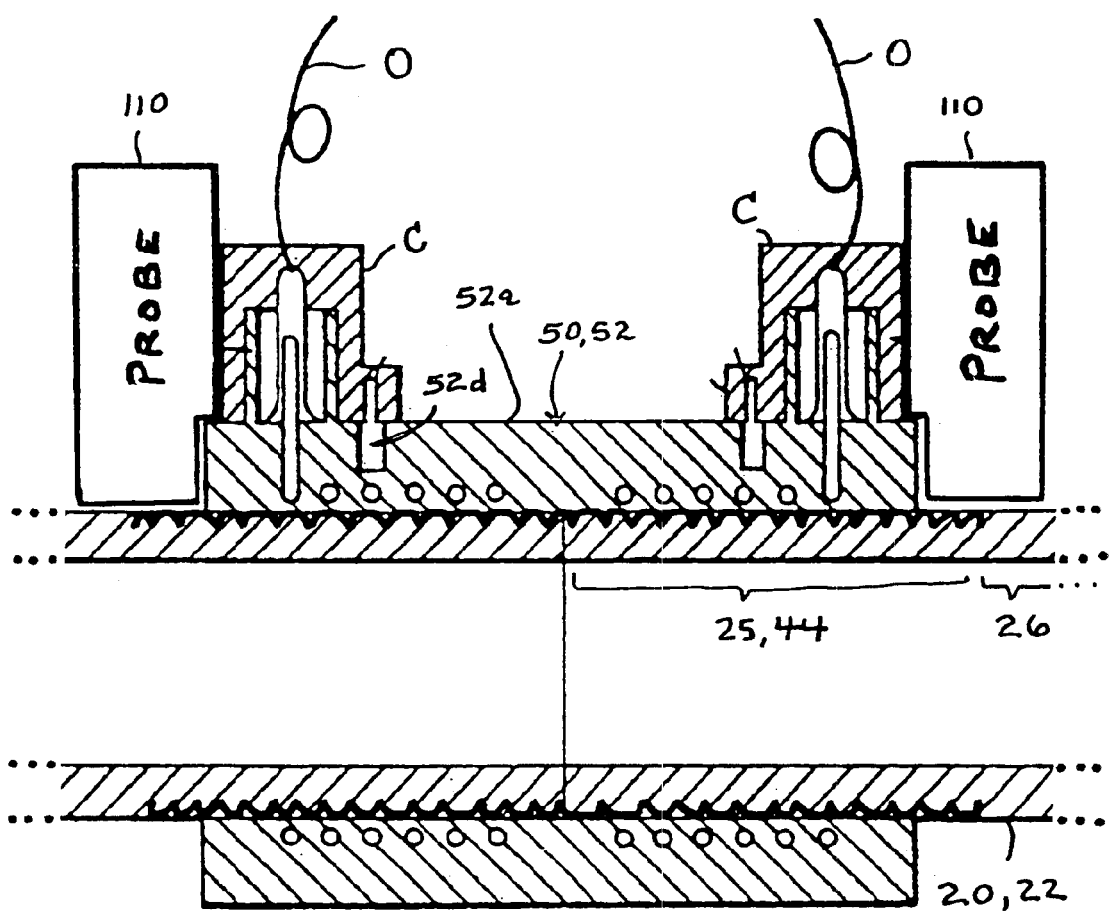
FIG. 5 is a is a side elevational view comparable to FIG. 4 except showing the connection of a pair of probe/connectors in accordance with the invention to the opposite terminals of the electrofusion fitting shown by FIG. 4.

FIG. 5 is a view comparable to FIG. 4 except showing the connection of a pair connectors "C" in accordance with the invention to the pair of opposite terminals 52c of the electrofusion fitting 52 of FIG. 4. The inventive connectors "C" generally combine conventional aspects of supplying power to the terminals 52c along with more particularly a pair of probes 110 in accordance with the invention for making an inventive surface-analysis determination precedent to electrofusion welding.

Figure 6:
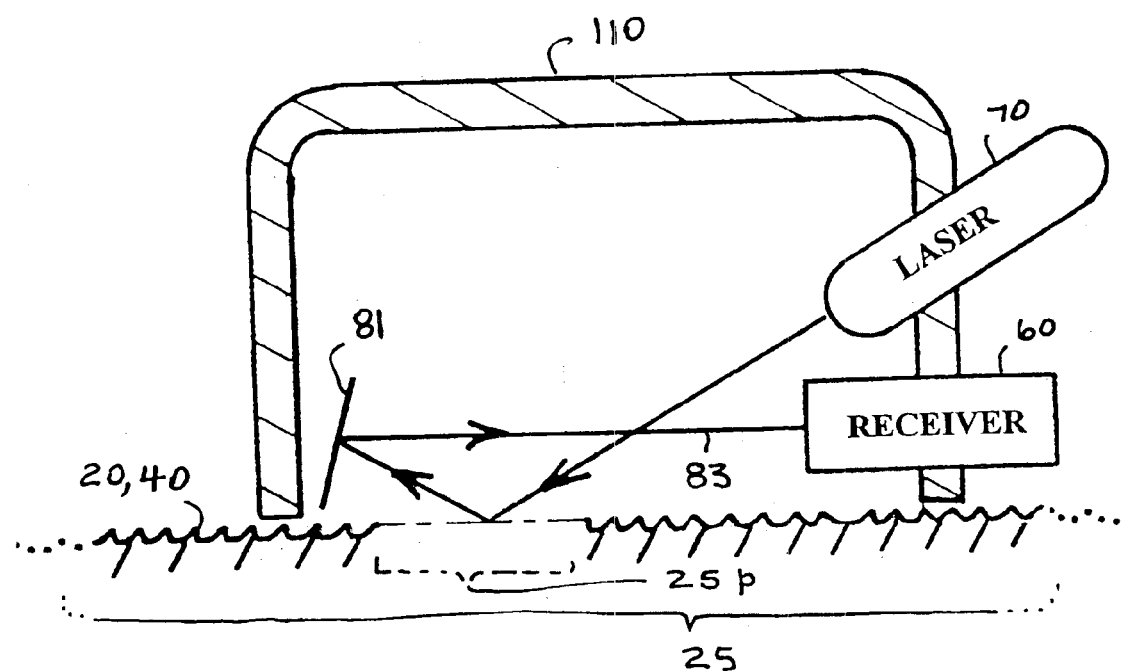
FIG. 6 is an enlarged detail of the right-side probe in FIG. 5 (eg., right relative FIG. 5's perspective) showing a non-contacting probe arrangement in accordance with the invention comprising an emitter (eg., "laser") and "receiver" for sensing quality of pipe surface matters such as the local presence or absence of sufficient scraping (or skinning) on the pipe exterior.

FIG. 6 shows better one preferred arrangement for the probe(s) 110 in accordance with the invention. The operative principle comprises measuring the reflection, or more accurately the change or loss of such, of an emitted signal as detected or collected by one or more signal receivers 60. Accordingly, the invention preferably operates on the basis of non-contact techniques.

As FIG. 6 more particularly shows, a signal emitter 70 comprises a laser source as, for example and without limitation, a diode laser operating on a six-hundred nanometer wavelength (eg., visible red light). The emission receiver 60 or collector optionally comprises an infrared/photo-transistor although alternatively a photo-diode works as well, and a photo-resistor presents another option still. One such group of usable devices include without limitation CdS cells (and as indicated 62 in FIG. 8).

It is preferred to aim the signal emitter 70 at as shallow angle-of-attack as possible, perpendicular to the ridges 40 of the scraped (or skinned) surface. To date the shallowest angle experimented with has been at 15° although it is believed that, if such can be constructed, half that angle would work better still. FIG. 6 shows that a patch 25p of the scraped surface 24, as illustrated by a dot-dash line, is impinged by the emitted signal. This patch, rather than being an infinitesimally small point, actually has some size. The impinged patch 25p has an ovate shape (if viewed from above) and impinges upon two to five or more lines of ridges 40. Arranging things for a shallower angle is better because correspondingly that means more lines of ridges 40 will obstruct or interfere with the 'clean' reflection of the emitted signal.

There are impediments to producing a probe 110 with as shallow angle as desired, and these impediments relate to physical problems when working at such a miniature scale. It is preferred to overcome such impediments by folding the signal with one or more mirrors 81 at least for the purpose of locating both the emitter 70 and collector 60 on the outboard side of the probe 110 where there is more physical space to mount such.

Figure 7:
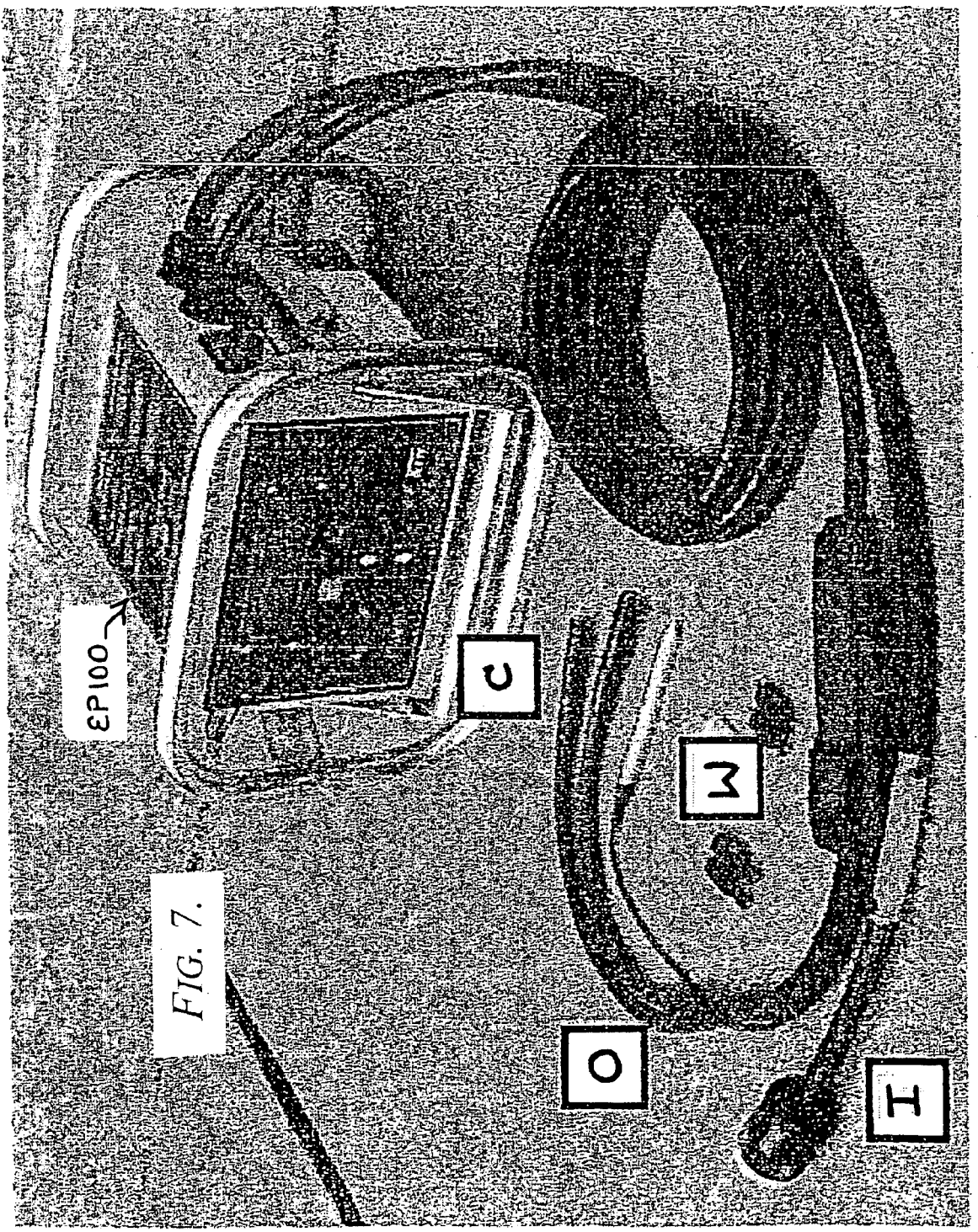
FIG. 7 is a perspective view of an electrofusion processor modified in accordance with the invention as more particularly described below.

FIG. 7 shows an electrofusion processor EP100 that is modified in accordance with the invention to include circuitry and controls 100 to obtain such functionality as machine-controlled determination of pipe surface quality preceding electrofusion of thermoplastics F100. The electrofusion processor EP100 comprises an input line cord "I," output leads "O," output lead connectors "C," bar-ode wand "W," and various connector adaptors not specifically referenced and partially covered by reference letter "W." The input line cord "I" plugs into something as public utility power which in this country runs at about one-hundred and twenty VAC line voltage. The electrofusion processor EP100 is configured (or programmed) for stepping through the functions of, among other functions, energizing the probe(s) 110 and analyzing the signal(s) obtained thereby in order to make a quality determination if the pipe surface(s) has(ve) been sufficiently scraped (or skinned or otherwise made suitable). This functionality is more particularly shown in Connection with FIGS. 8 and 9. Other functionality which is extra for the purpose includes without limitation data-logging functions F101 which record and store operator functions against a time and date stamp in order to allow 'ad hoc' auditing of operator honesty and/or integrity. It is an object of the invention that, in cases of a failing surface-analysis determination, the electrofusion processor EP100 is aborted or disabled A120 from any chance at welding F250 until a passing surface-analysis determination is obtained A125. Presumptively a passing surface-analysis determination A125 can only practicably be obtained by an operator performing a reasonably timely calibration A130 (see FIG. 9) and then, after that, obtaining a very recent passing surface-analysis determination A125 (see FIG. 10) prior to a fusion operation F250. Instances of failing surface-analysis determination to date are presumptively/preferably overcome by an operator (or worker) disassembling the fitting and pipe(s) A135 in order to scrape or re-scrape A140 (skin or re-skin or the like) the involved pipe surface(s) for a succeeding chance to obtain a passing surface-analysis determination A125.

Figure 8:
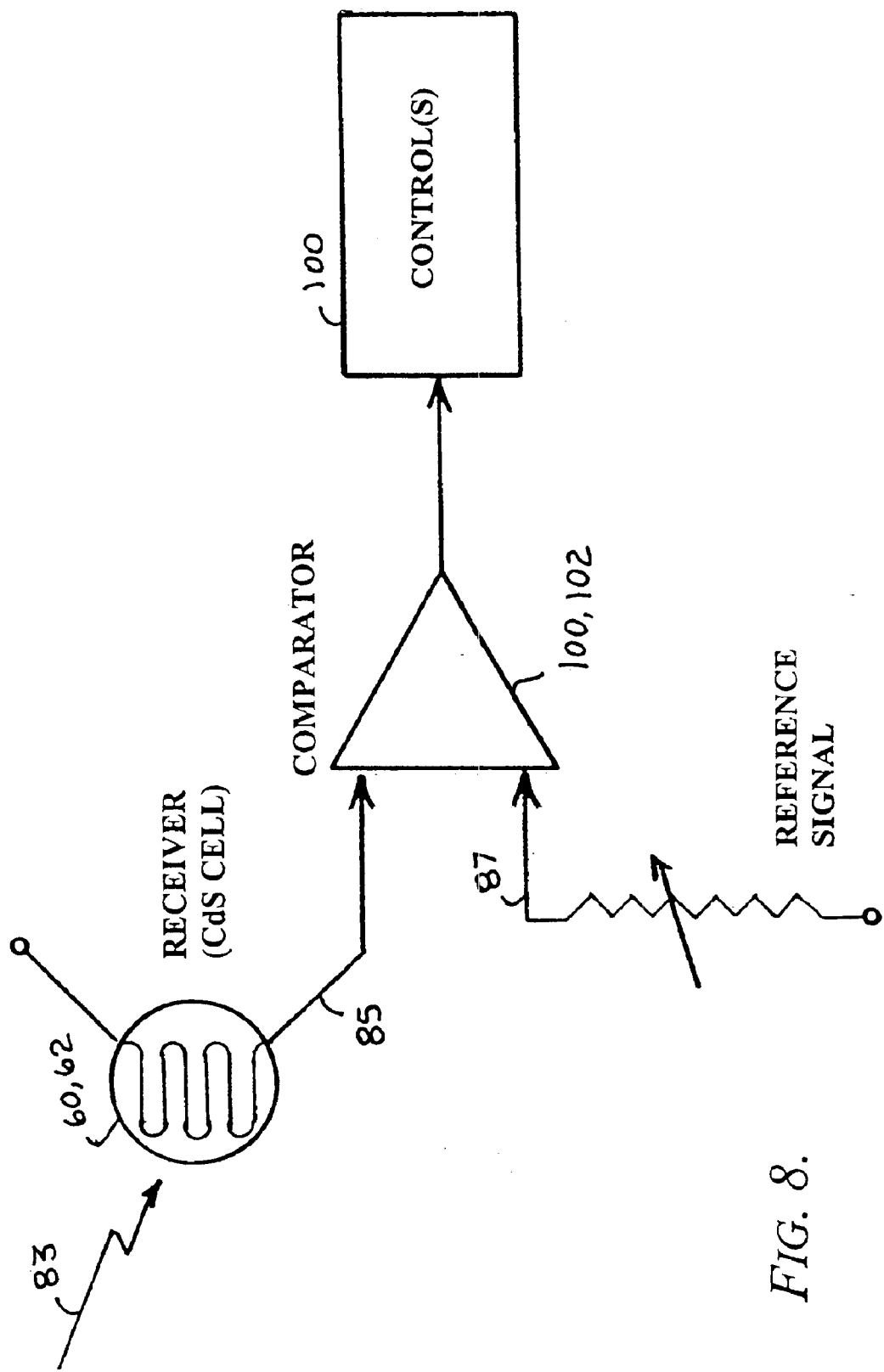
FIG. 8 is a is schematic view of a preferred embodiment of the invention for utilizing the results of surface analysis preceding electrofusion of thermoplastics in accordance with the invention.

FIG. 8 is a is schematic view of a preferred embodiment of the invention for utilizing the results of surface analysis preceding electrofusion of thermoplastics in order to determine passing or failing surface-analysis determination. The receiver 60 is shown receiving the received signal 83, wherein FIG. 6 shows a preferred arrangement for positioning a signal receiver 60 in accordance with the invention relative to a surface-to-be-analyzed and the source 70 of such signal, a signal emitter in accordance with the invention. The receiver 60 provides its own output-signal 85 corresponding to the received signal 83. The receiver's output signal 85 is fed to a comparator 102 (eg., 'comparison operator' or like op-amp) which compares the receiver's output signal 85 to a reference signal 87. At present it is preferred if the comparator 102 provides an output which signifies "pass" or "fail" although it is more preferred still if the comparator 102 outputs a range of values corresponding to a range of quality findings (eg., ranging from an upper extreme of fairly superior to a lower extreme of fairly inferior). The output of the comparator 102 is fed to control system 100, as shown generically in FIG. 8. The control system 100 operates to achieve several functions. One, the control system 100 disables the operability of the weld function F250 of the electrofusion processor EP100 until a timely "pass" surface-analysis is achieved. Another, the control system 100 provides a recordable activity F101 for the data-logger to record so that a relatively permanent record is made of the "pass", "fail" and/or 'degree' (or other) determination for audit purposes. Additionally, the control system provides the operator with one or more feedback signals so that the operator can act to correct the situation accordingly.

Preferred at present and due to changing preference in the future, it is preferred to compare the received (or measured) signal 83 against a reference signal 87 in order to make a "pass" or "fail" (or in-between quality) surface-analysis determination F100 in accordance with the invention. It is known, however, in fields of industry outside the invention to utilize multiple metrics and/or criteria to make a surface-analysis evaluation, such as disclosed by and without limitation Lasercheck® gauge of the Optical Dimensions Co., of Lake Forest, Calif. Ideally it might be desirable to utilize the most advanced technology available to make a most complete surface-analysis determination. But in the real world of protecting against human error in electrofusion practice it is more realistic to practice technology which is highly competent though not the most advanced for the purposes of making a "pass" or "fail" (or in-between) surface-analysis determination precedent to electrofusion. It is believed that utilizing highly-competent in contrast to the most-advanced technology is more practical when better opportunity for advancing the objects of the invention are to be obtained from analyzing a larger area/circumference of the pipe(s).

Figure 9:
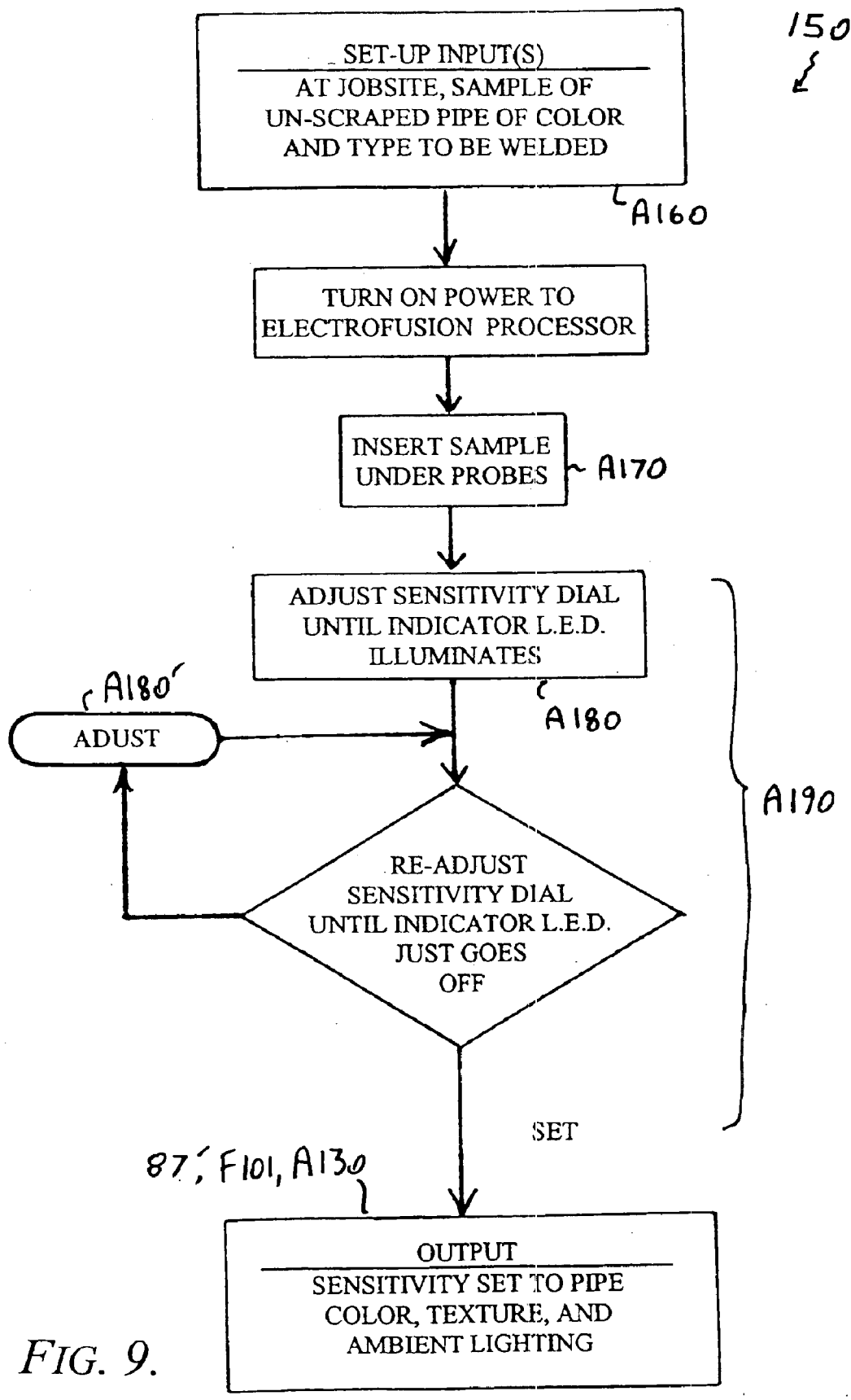
FIG. 9 is a flowchart showing a method in accordance with the invention for determining a particular "reference signal" as denominated in FIG. 8.

FIG. 9 is a flowchart showing a methodology 150 in accordance with the invention for determining a particular "reference signal" 87 as denominated in FIG. 8. FIG. 9 represents what might be alternatively referred to as a 'set-up' or a 'calibration' process 150. An operator at the job-site fetches or acquires a sample piece of the pipe(s) to be-welded. The object is to determine what signal the un-scraped (or un-skinned or otherwise un-cleaned) pipe provides under local conditions. Local conditions include color and type of pipe to-be-welded as well as the ambient light (in spite of shielding or hooded-enclosures to block out ambient light). Preferably this calibration or set-up cycle would likewise be logged by the data-recorder 100 for audit purposes F101 to determine irregularities and the like.

Step one A160 involves the operator procuring a sample of the un-scraped (or un-skinned or insufficiently cleaned) pipe of the color and type to-be-welded before the welding process(es) are to be attempted. It is preferred if this step is done often. For example, a work day which will involve a lot of welding of the same type and color of pipe deserves calibration at least at the beginning of the day. Indeed the calibration process 150 might best be performed several times during a day as there are likely changing circumstances with the quality of the pipe or else the amount of leakage of ambient light. In contrast, with reference to FIG. 6, the diminishment of the received signal 83 as compared to a reference 87 of un-scraped (or un-skinned or insufficiently cleaned) pipe against scraped (or its corollary sufficiently skinned or cleaned) pipe is ordinarily substantial:— particularly for yellow and white pipe, yellow pipe being more common in natural gas piping.

A succeeding step A170 involves inserting one or more samples of un-scraped (or insufficiently skinned or cleaned) pipe under the probes 110 to obtain A190 a reference value 87 or {87}. Perhaps one sample is sufficient to obtain the reference value. Better yet is if the operator subjects several samples to the work of the probes 110 to provide several individual reference values 87, and with which the processor 100's control circuitry analyzes for determining a 'statistical' reference value {87}. FIG. 9 shows a manual way A180 of determining individual reference values 87, as by an operator manually tuning a dial as to a variable resistor (or potentiometer) or the like until such activity A190 finds a given level of diminishment of the received signal 83 in comparison to the emitted signal. The foregoing assumes the circuitry 100 is measuring signal strength.

Ultimately, by means of the foregoing, the operator establishes a reference value 87 which compares favorably to what un-scraped (or insufficiently skinned or cleaned) pipe 20 looks like.

Figure 10:
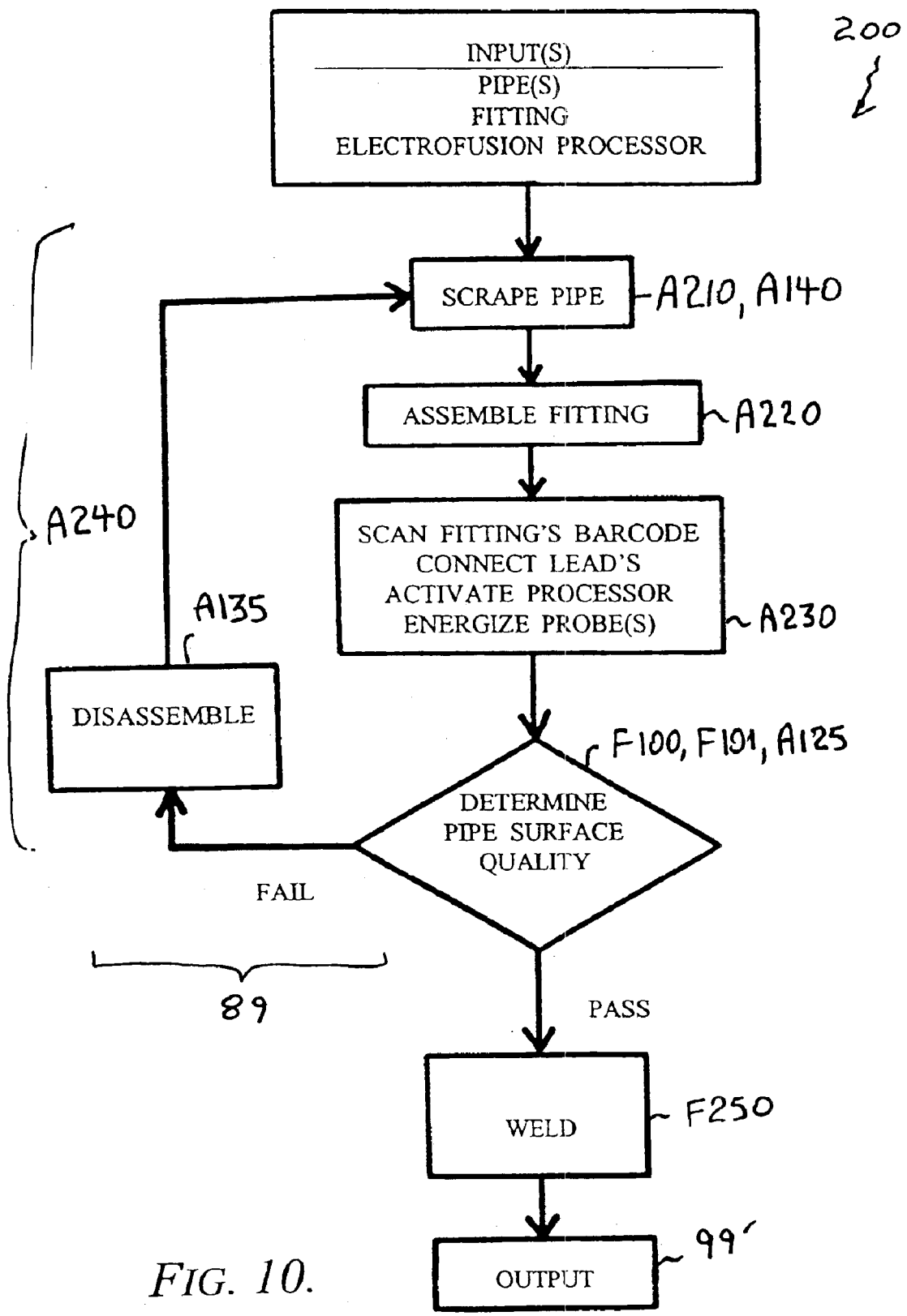
FIG. 10 is a flowchart showing a method in accordance with the invention for determining passing or failing pipe surface quality preceding electrofusion welding of thermoplastics in accordance with the prior art.

FIG. 10 is a flowchart showing a further methodology 200 in accordance with the invention for determining F100 passing or failing pipe surface quality preceding electrofusion welding. The presumptive input or starting materials (and apparatus) include an electrofusion processor EP100 or probe-operating/signal-processing system 100 in accordance with the invention, a fitting 50 and one or more pipes 20 depending on whether it is a single pipe to-be-welded to (eg, in cases of a tapping-tee fitting 51) or more (eg., in cases of a coupling fitting 52). Step one A210 preferably comprises the original attempt to satisfactorily scrape (or skin or clean) the involved pipe section(s) prior to welding. Step two A220 presumptively comprises assembling the fitting where it belongs. The succeeding steps A230 comprise variously inputting to the electrofusion processor the particulars of the particular fitting:—nowadays that being most popularly accomplished by bar-code coding affixed to the fitting in combination with equipping the electrofusion processor with a bar-code reader (eg., "W" in FIG. 7). It is presumed that the fitting's welding particulars will be a relevant factor in surface-analysis evaluation, but then perhaps not. What is presumptively most relevant is whether the relevant pipe section(s) has(have) been properly scraped (or otherwise skinned or cleaned).

Provided that the fitting 50 is properly disposed on the presumptively-properly scraped (or skinned or cleaned) pipe section(s) 25, a preferred succeeding step A230 is to energize the probe(s). It is preferred that the electrofusion processor EP100 be disabled A120 from providing welding-power to the fitting 50's terminals unless as a condition precedent the electrofusion processor is enabled to do so by the probe control circuitry. Therefore, energizing the probes 10 for the first time affords the first opportunity to get an "operative" feedback signal 89. In contrast, if a "fail" (or "abort" or "disable") feedback signal is obtained, the operator is faced with several choices A240. Perhaps the fitting was improperly aligned over properly scraped (or skinned or cleaned) pipe section. Re-alignment might solve the problem. Perhaps otherwise, the pipe section(s) is(are) indeed insufficiently scraped (or skinned or cleaned), and therefor the operator's only practical choice for remedy is to disassemble and re-clean (eg., scrape or skin) the involved pipe section as whole.

Such is done iteratively until ultimately a "pass" (or the like) signal 89 is obtained from the probe(s) 110's processing/control circuitry 100. Given satisfaction of the foregoing condition(s), the probe(s) 110's processing/control circuitry 100 enables (eg., no longer aborts or disables) the electrofusion processor EP100's weld functions F250 (eg., the power-supply feed to the terminals). Therefore a better likelihood of a satisfactory weld in accordance with OEM prescriptions is much more likely obtained. The invention offers the prospect of negating human error better than nowadays achieved by previously practiced practices in the field of electrofusion of thermoplastics.

Figure 11:
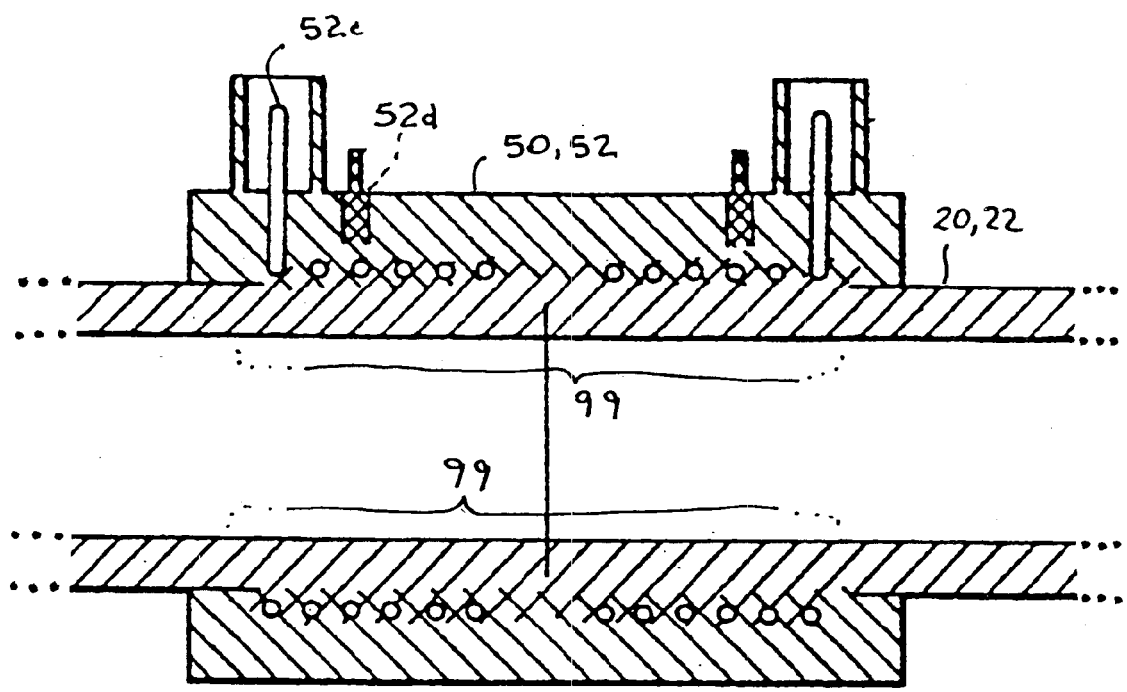
FIG. 11 is an elevational sectional view comparable to FIG. 4 except showing successful completion of electrofusion welding of the pipe ends and coupling.

FIG. 11 is sectional view comparable to FIG. 4 except showing successful completion of electrofusion welding 99 of the pipe ends 22 and coupling 52. It is an object of the invention to promote a better likelihood of achieving satisfactory welds by a machine "checking" of the condition of things precedent before welding is attempted, as well as by providing a data log of such, for auditing purposes, not as much for back-tracking to identify operators lacking integrity but more for the benign purpose of reminding operators persistently that there is log of their operations. To be abstract for a moment, a popular definition of integrity is not only that one would do as one would want for themselves but alternatively that one would "do" with the thought that someone else is watching over one's shoulder. Every action will be public, or at least exposed in the end. The data logging functions of the invention promote the concept of that "someone" else is indeed watching over one's shoulder. It's not so much an object of the invention to create an onerous "big brother," but that given good people who work as operators, who are nevertheless pressured by productivity pressures, better it is to promote good work ethics for the larger good of public welfare or safety than to rush a job and endanger such for sake of meeting productivity targets. Given that many of the many of these electrofusion welds are made in natural gas pipelines, the stakes are paramount. It is not so much a matter of assuring no contractor forsakes its/his responsibility but that no contractor endangers the public needlessly beyond what are locally-stated or more broadly-codified acceptable criteria for constructing electrofusion-formed piping systems.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

I claim:

1. A method comprising a surface-analysis determination precedent to electrofusion welding, in which a pipe or pipes to-welded to an electrofusion fitting are prescribed to be scraped or skinned to remove contaminants, comprising the steps of:

supplying raw, or not-skinned in recent times, pipe stock for an electrofusion welding operation;

scraping or skinning an applicable section of the pipe contemporaneously prior to performing the electrofusion welding operation;

suppling an electrofusion fitting and electrofusion processor for completing electrofusion welding of said electrofusion fitting to the applicable section of said pipe if such is passable for the purpose;

providing at least one non-contact probe for inspecting the applicable pipe section contemporaneously after the step of scraping or skinning;

feeding the output of the at least one non-contact probe to control circuitry to determine alternately a "pass" condition which enables operation of the electrofusion processor, and hence welding, or alternatively disables operation of the electrofusion processor until the at least one probe is disassembled and then re-assembled for a successive measurement so that presumptively during the interim an operator can re-attempt to skin or scrape the applicable pipe section anew in order to obtain a "pass" condition.

* * * * *